(12) United States Patent
Mudry et al.

(10) Patent No.: US 7,806,010 B2
(45) Date of Patent: Oct. 5, 2010

(54) TEST PORT ASSEMBLY FOR ALLOWING A TEST PROBE TO BE INSERTED INTO A CONDUIT

(75) Inventors: Robert G. Mudry, Plymouth, MI (US); Matthew M. Fleming, Ypsilanti, MI (US); Bruce Delvin, Brighton, MI (US)

(73) Assignee: Electric Power Research Institute, Inc., Charlotte, NC (US)

( * ) Notice: Subject to any disclaimer, the term of this patent is extended or adjusted under 35 U.S.C. 154(b) by 385 days.

(21) Appl. No.: 12/048,497

(22) Filed: Mar. 14, 2008

(65) Prior Publication Data
US 2009/0229385 A1     Sep. 17, 2009

(51) Int. Cl.
G01D 21/00 (2006.01)
G01N 1/16 (2006.01)
G01N 1/26 (2006.01)

(52) U.S. Cl. .................................. 73/866.5; 73/863.82
(58) Field of Classification Search ............... 73/866.5, 73/863.85, 863.82
See application file for complete search history.

(56) References Cited
U.S. PATENT DOCUMENTS
2,864,254 A * 12/1958 McDonald et al. ....... 73/863.73
3,260,120 A * 7/1966 Stilwell .................. 73/863.54

OTHER PUBLICATIONS

"Coal—Sampling of Pulverized Coal Conveyed by Gases in Direct Fired Coal Systems", International Standard, Dec. 15, 1991, pp. 1-18, vol. 9931.
"Coal Pulverizers", American Society of Mechanical Engineers, 1969, pp. 1-26.
"EPRI Coal Flow Loop", Electric Power Research Institute, Inc., Mar. 2004, pp. 3-1 through 3-15.
"EPRI Coal Flow Loop, Evaluation of Extractive Methods", Mar. 2005, pp. 3-1 through 3-5 and 6-1 through 6-3.

* cited by examiner

*Primary Examiner*—Hezron Williams
*Assistant Examiner*—Nathaniel Kolb
(74) *Attorney, Agent, or Firm*—Trego, Hines & Ladenheim, PLLC (57) ABSTRACT

This invention relates to a rotating test port assembly for measuring air flow and particulate matter in conduits. The test port assembly includes a first end section, a second end section, and a rotating section adapted for rotation between the first and second end sections. The assembly further includes a test port positioned on the rotating section for allowing a test probe to be inserted into a stream flowing in a conduit.

14 Claims, 7 Drawing Sheets

TEST PORT ASSEMBLY FOR ALLOWING A TEST PROBE TO BE INSERTED INTO A CONDUIT

BACKGROUND OF THE INVENTION

The present invention relates generally to an apparatus and method for measuring airflow and particulate matter, and more particularly to a rotating test port assembly for measuring air flow and particulate matter in conduits.

The measurement of air flow and particulate matter in a conduit, such as piping, is of great importance to facilities such as power plants where environmental and operational efficiency are of concern. Currently, power plants use a manual measurement process to determine the air flow and the amount of particulate matter contained therein flowing through a conduit. This is done by inserting a test probe device through one or more test ports. The test ports, typically two to four, are welded directly to the conduit to allow the probe to be inserted into a stream of air and particulate matter flowing through the conduit. Typically, a standard ball valve is connected to each of the test ports to allow a user controlled access to the stream. When access is desired, the ball valve is opened and the test probe is inserted therethrough. When testing is finished, the test probe is removed, and the ball valve is closed to prevent the stream from exiting the conduit through the test port.

However, the current measurement process has limitations and can often result in erroneous measurements because the probe only traverses a straight line and portions of the flow area are not measured. Since portions of the flow area are not measured, these portions are assumed for calculating the true flow rate of air in the conduit, thereby resulting in errors. If a two-phase flow of air and particulate matter is being measured, both the air velocity and the particulate flow measurement are affected resulting in degradation of these assumptions and causing even greater errors. Through testing, it has been found that the error in particulate matter measurement may be as high as thirty-five percent of the true flow rate.

One way to combat these errors is to increase the number of test ports on the conduit; however, there are limitations to the number of test ports that can be installed due to the size of the conduit, the material of the conduit, and the service the conduit is being used in. For example, conduits used in corrosive environments may have ceramic linings which limit the number of test ports that can be installed.

Another solution used to reduce measurement errors is to use an articulated test probe that allows a tester to take a measurement in a pattern other than a straight line and, thus cover more of the cross sectional area of the conduit. However, these probes have limitations that affect their accuracy and that cannot easily be corrected or even determined. For example, one of the more common articulated probes has multiple extraction nozzles that draw in particulate matter simultaneously. However, in certain conduit configurations and flow conditions the multiple nozzles may not sample equally. Also, because these probes have moving parts and seals, there is potential for leakage in the sample lines that can adversely affect the measurements. In some instances, the articulated probes become jammed inside the conduit which makes their retrieval from the sampling line difficult. In other instances, the articulated probes, which have a much more complex internal flow path, may become plugged because of moisture content in the sampling stream therefore voiding the measurement.

BRIEF SUMMARY OF THE INVENTION

These and other shortcomings of the prior art are addressed by the present invention, which provides a rotating test port assembly for accurately measuring air and particulate matter flow in a conduit.

According to one aspect of the present invention, a test port assembly includes a first end section, a second end section, a rotating section, and a test port. The rotating section is adapted for rotation between the first and second end sections. The test port is positioned on the rotating section to allow a test probe to be inserted into a stream flowing in a conduit.

According to one aspect of the present invention, a test port assembly adapted for replacing a portion of a conduit includes a first end section, a second end section, a rotating section, and a test port. The first end section is connected to a first end of the conduit. The second end section is connected to a second end of the conduit. The rotating section is positioned and adapted for rotation between the first and second end sections, and the test port is positioned on the rotating section to allow a test probe to be inserted into a stream flowing in the conduit.

According to another aspect of the present invention, a method for testing a stream in a conduit includes the steps of replacing a section of the conduit with a test port assembly having a first end section, a second end section, a rotating section positioned between the first and second end sections, and a test port positioned on the rotating section. The method further includes the steps of inserting a test probe into the test port until the probe is positioned at a desired location within the stream, and rotating the rotating section to extract data from the test probe at various data points within the conduit.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
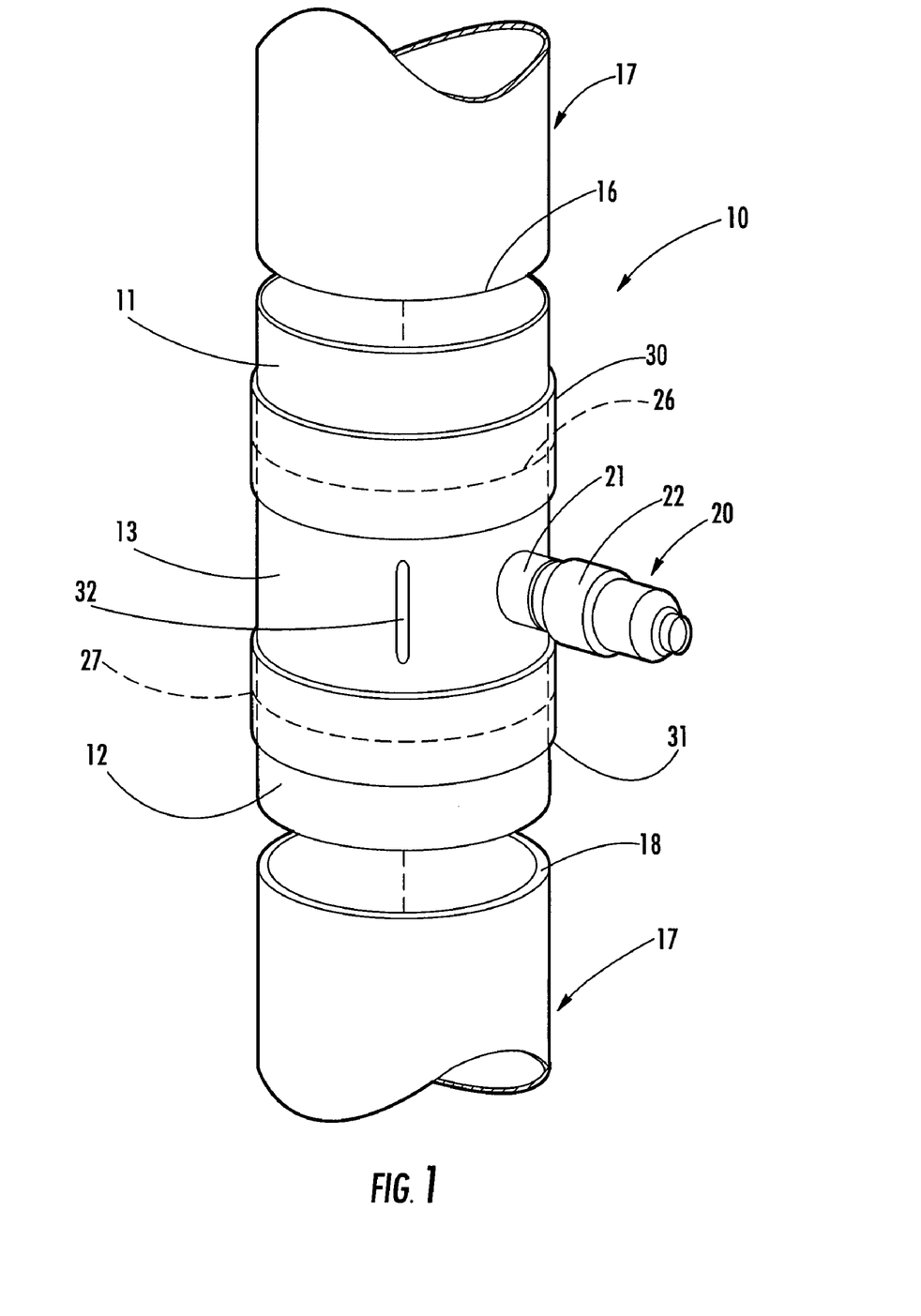
FIG. 1 shows a rotating test port assembly according to an embodiment of the invention.
Figure 2:
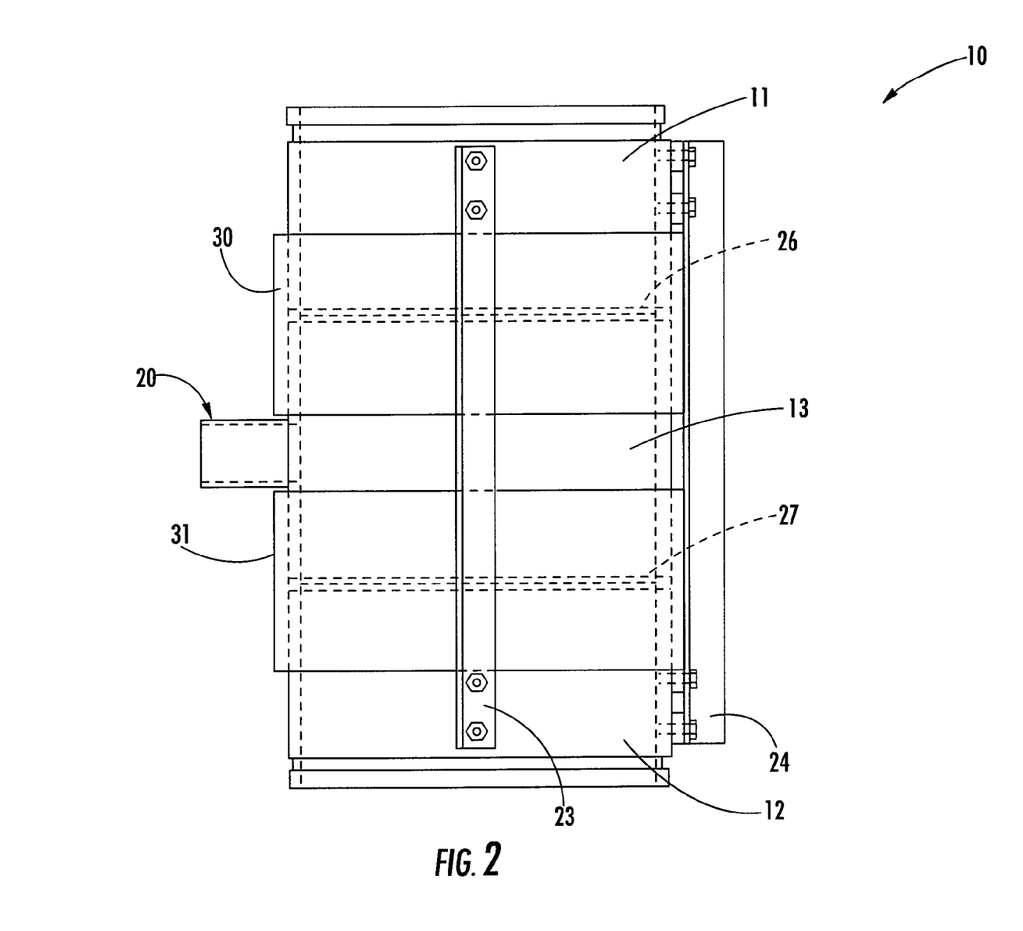
FIG. 2 is a cross-sectional view of the test port assembly of FIG. 1.

Referring to the drawings, an exemplary rotating test port assembly according to an embodiment of the invention is illustrated in FIGS. 1 and 2 and shown generally at reference numeral 10. The test port assembly 10 includes a first end section 11, a second end section 12, and a rotating section 13 positioned and adapted for rotation between the first and second end sections 11 and 12.

As shown, the first and second end sections 11 and 12 are adapted to be attached to a first end 16 of a conduit 17 and a second end 18 of the conduit 17, respectively. The first and second end sections 11 and 12 may be attached to the first and second ends 16 and 18 using various methods. For example, the ends could be welded (including the use of adhesive for plastic conduits) together, each of the ends could have flanges to allow the ends to be bolted together, or as shown in FIG. 2, the ends could be grooved to allow the use of pipe couplings.

A test port 20 is positioned on the rotating section 13 to allow the insertion of a test probe (not shown). The test port 20 allows a test probe to access a stream of air, particulates, or fluid flowing within the conduit 17 to extract measurements therein. The test port 20 may be formed of a short piece of conduit 21 and a valve 22, such as a ball valve, to allow the test probe to be inserted therethrough and to prevent the stream from exiting the test port 20 when not being used. Other configurations could also be used so long as the test port 20 is capable of allowing the test probe to be inserted therethrough and capable of closing to prevent the stream from exiting through the test port 20.

Supports 23 and 24 are connected to the first and second end sections 11 and 12 to provide stability to the assembly 10 and assure that the rotating section 13 is secured for rotation between the first and second end sections 11 and 12. It should be appreciated that the supports may be placed at various positions around the assembly 10 to not only provide adequate support, but also to create different degrees of rotation for the test port 20.

Joints 26 and 27 are formed between the first end section 11 and the rotating section 13 and between the second end section 12 and the rotating section 13. The joints 26 and 27 allow the first end section 11, the rotating section 13, and the second end section 12 to be properly aligned and are adapted to allow the rotating section 13 to rotate between the first and second end sections 11 and 12. Seals 30 and 31 are wrapped around the joints 26 and 27, respectively, to prevent the stream flowing through the assembly 10 from escaping through the joints 26 and 27. In this example, the seals are a rubber boot type seal, but any suitable seal type and material could be used.

Figure 7:
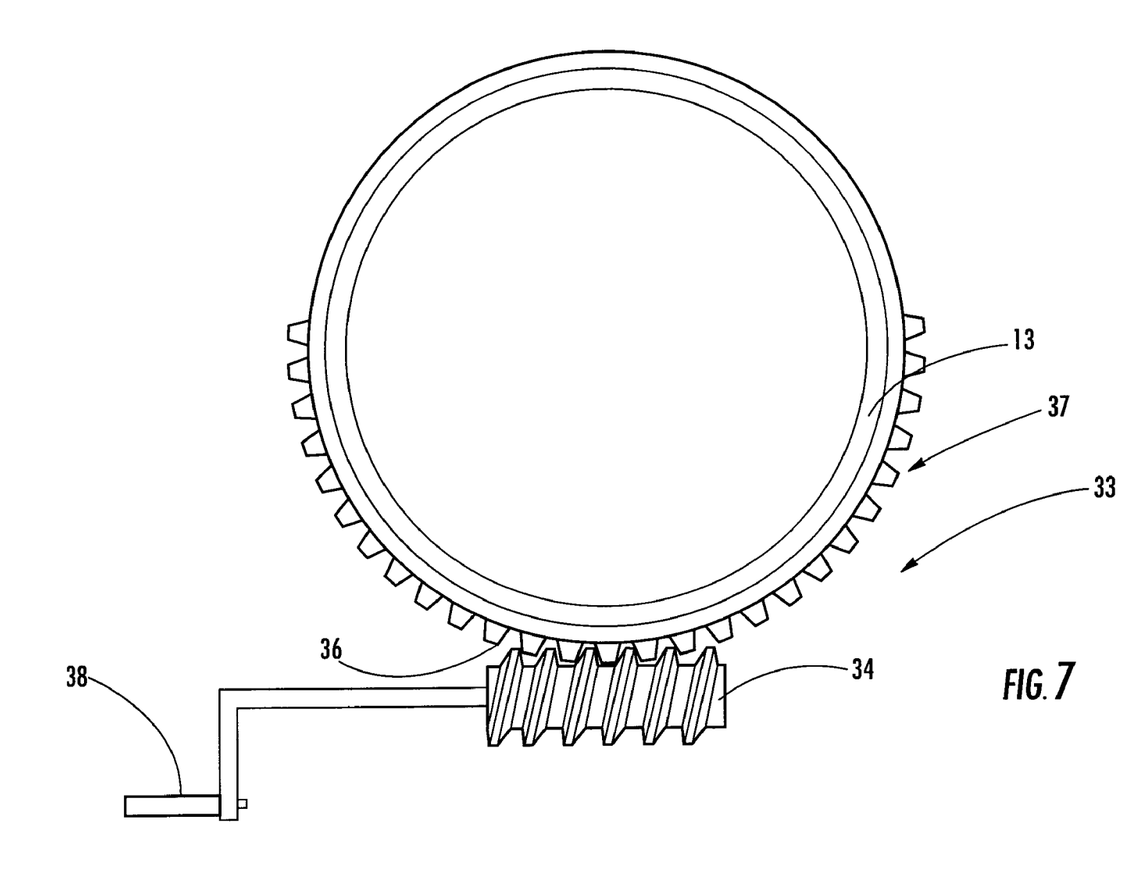
FIG. 7 shows a gear arrangement for use on the test port assemblies of FIGS. 1, 3, and 5.

In use, the conduit 17 is cut to remove a section of the conduit 17 and allow the assembly 10 to be inserted in its place. As discussed above, the assembly may be attached to the conduit by welding, flanges, couplings, or any other suitable method. Once the assembly 10 is secured in the conduit 17, measurements of the stream flowing through the conduit may be taken. The measurements are taken by inserting a test probe into the test port 20 until the test probe is positioned into the stream at a desired position within the conduit 17. Once the test probe is inserted into the stream, tests can be performed at various test points within the conduit 17 by rotating the rotating section 13. This can be done by using a handle 32 positioned on the rotating section 13, as shown in FIG. 1, or by a gear set 33, shown in FIG. 7. As shown, the gear set 33 uses a worm gear 34 to interact with teeth 36 of a gear 37 positioned on the rotating section 13. It should be appreciated that any suitable type of gears for rotating the rotating section 13 could be used. As shown, the gear set 33 is operated by a hand crank 38; however, the gear set 33 may also be actuated by an electric motor, pneumatics, or any other suitable actuator.

Figure 3:
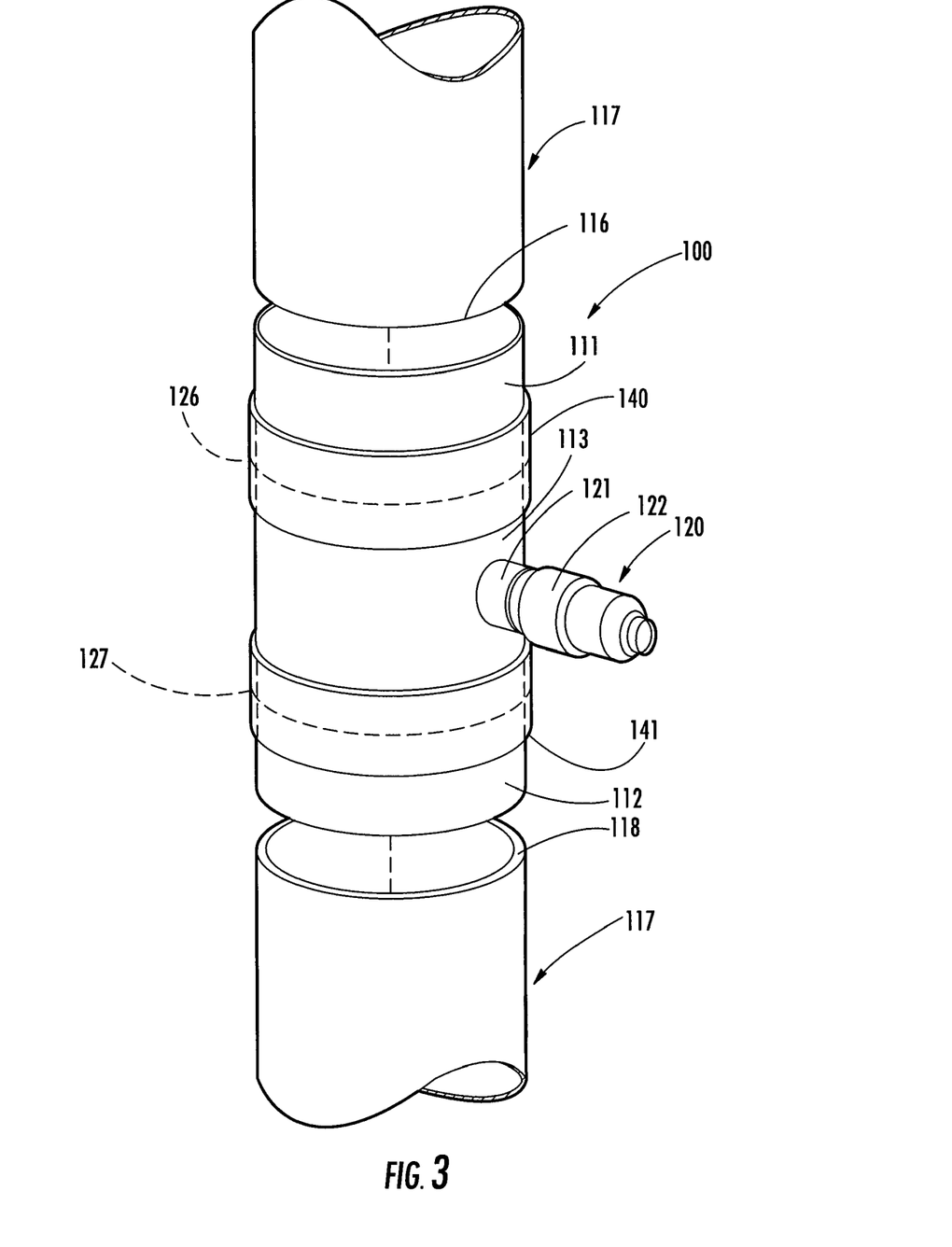
FIG. 3 shows a rotating test port assembly according to an embodiment of the invention.
Figure 4:
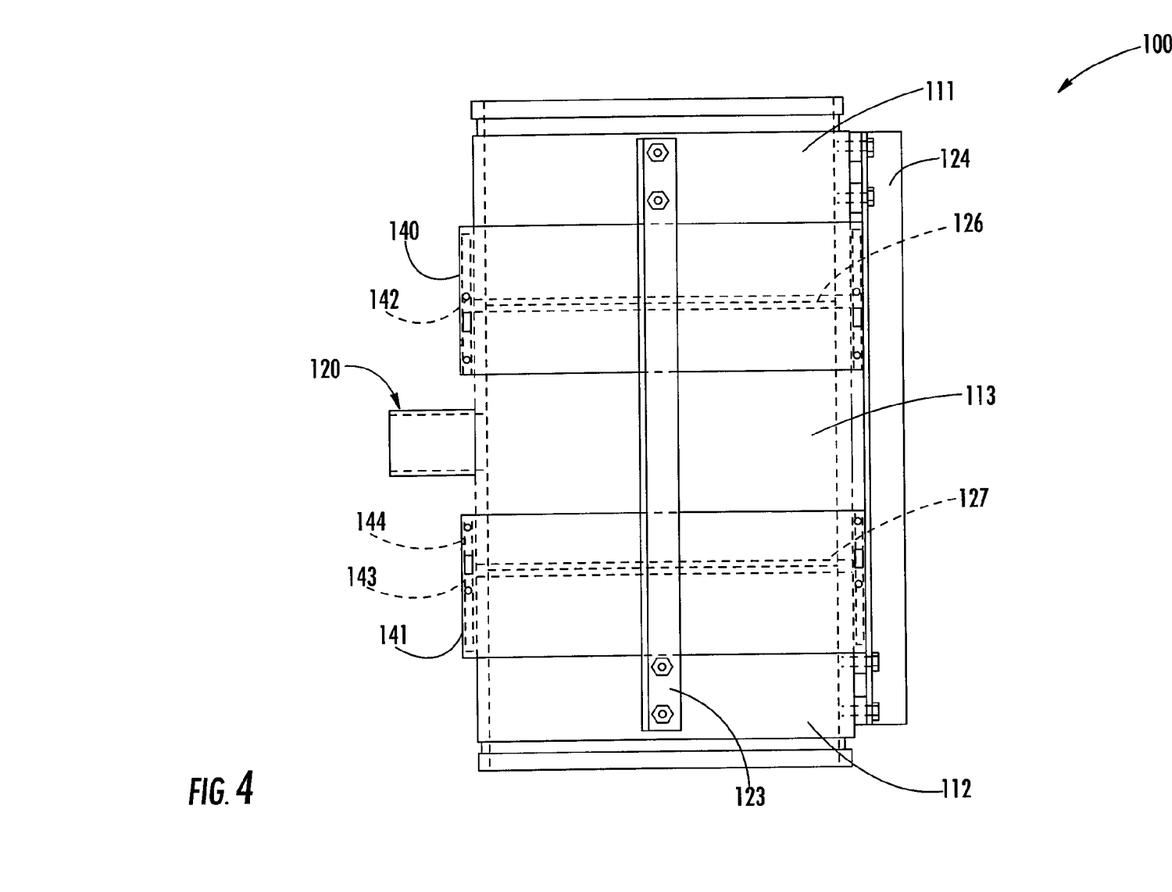
FIG. 4 is a cross-sectional view of the test port assembly of FIG. 3.

Referring to FIGS. 3 and 4, a test port assembly 100 according to another embodiment of the invention is shown. The test port assembly 100 is similar to the test port assembly 10 in that it includes first and second end sections 111 and 112, a rotating section 113, and a test port 120 having a valve 122. The test port assembly 100 is also installed and operated like test port assembly 10. Unlike test port 10, test port assembly 100 includes a sleeves 140 and 141 and o-ring seals 142 and 143.

The sleeves 140 and 141 are connected to the first and second end sections 111 and 112, respectively, and provide additional support to the assembly 100, as well as aid in the alignment of the end sections 111 and 112 and the rotating section 113. The sleeves 140 and 141 may be integrally formed with the end sections 111 and 112 or may be attached to the end sections 111 and 112 by welding, or any other suitable method to provide a sealed and secure attachment. The o-rings 142 and 143 provide a seal between the rotating section 113 and the sleeves 140 and 141, respectively, to prevent leakage of the stream flowing through the assembly 100.

A seal air port 144 may also be used in the assembly 100 to provide additional sealing capabilities and to prevent particles from entering between the sleeves 140 and 141 and the rotating section 113, thereby preventing particulate matter from interfering with rotation of the rotating section 113.

Figure 5:
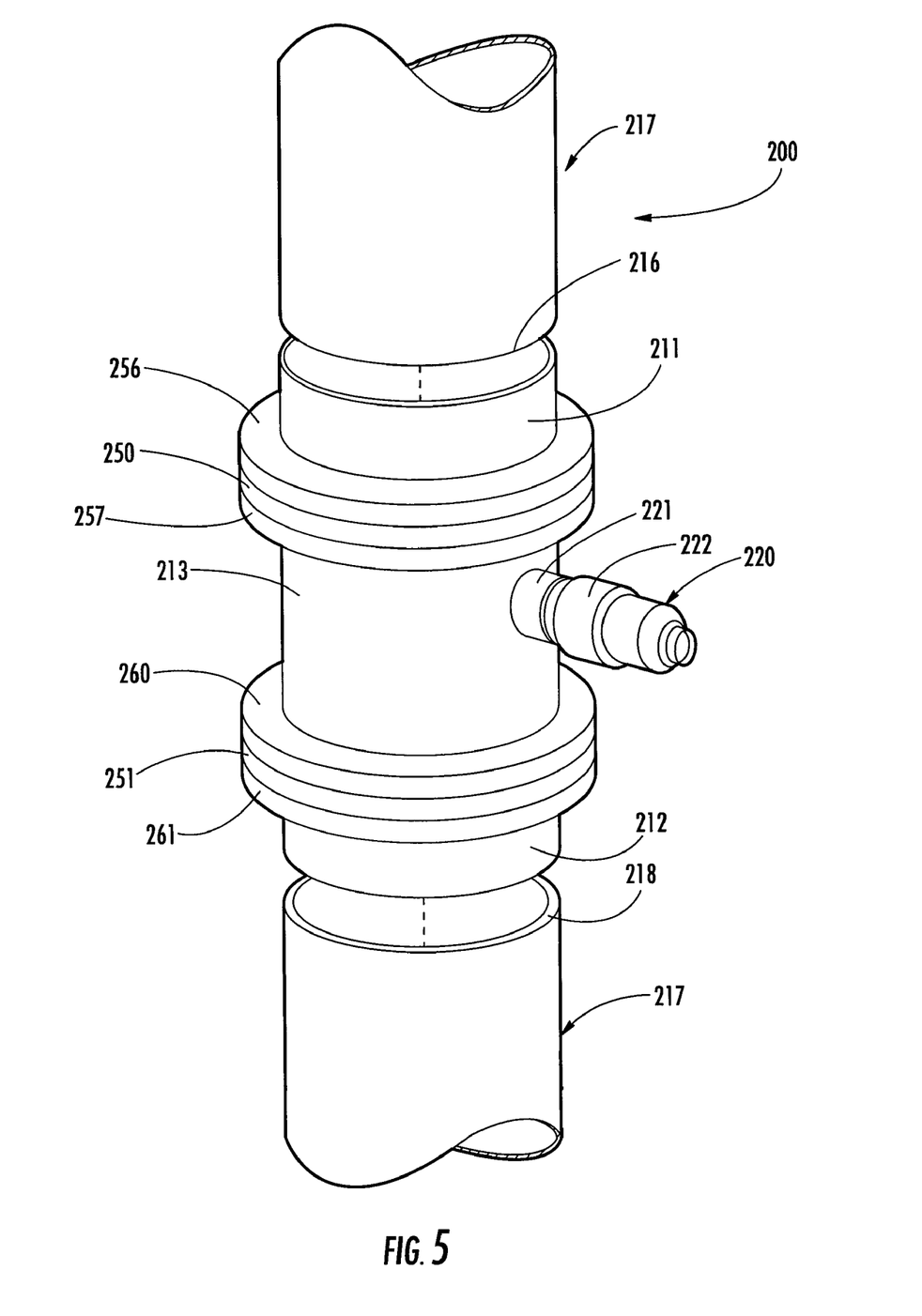
FIG. 5 shows a rotating test port assembly according to an embodiment of the invention.
Figure 6:
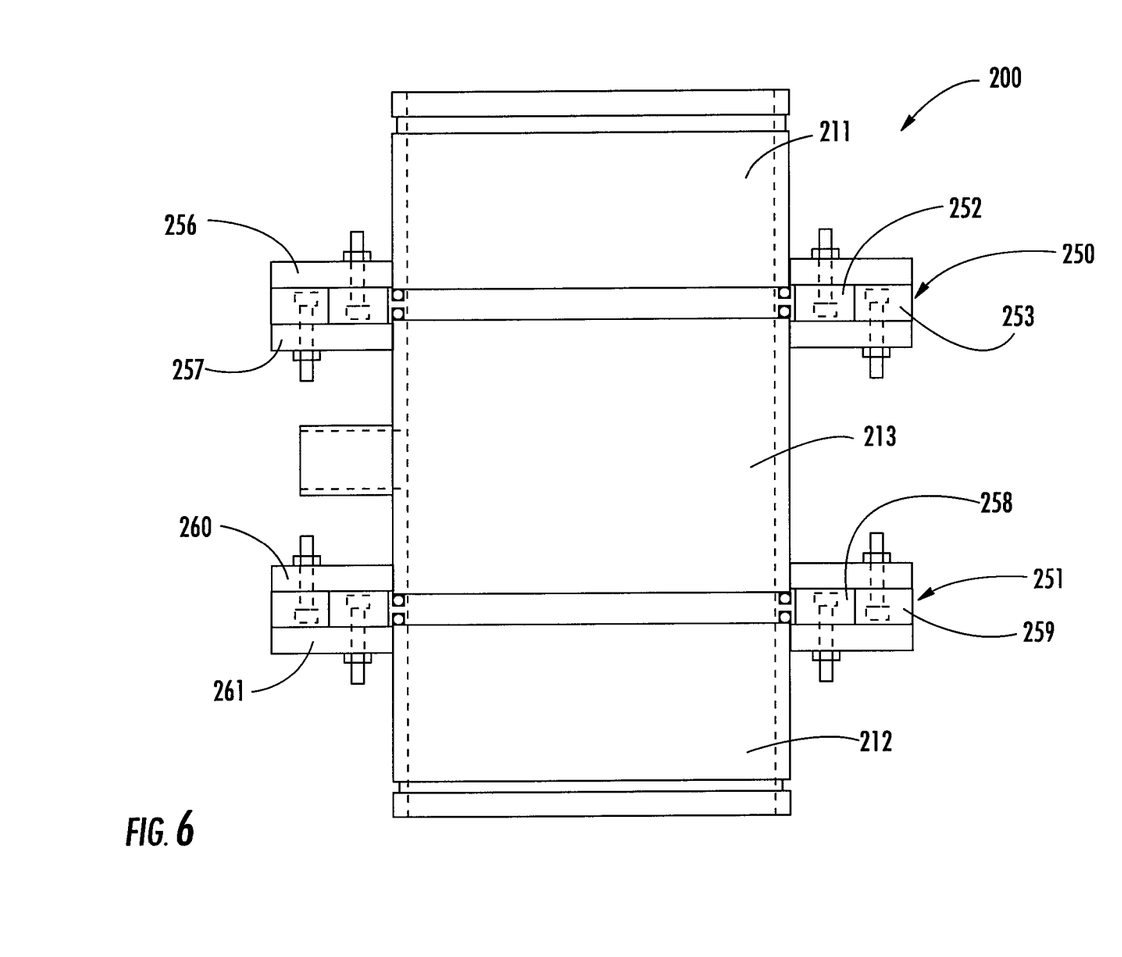
FIG. 6 is a cross-sectional view of the test port assembly of FIG. 5.

Referring to FIGS. 5 and 6, a test port assembly 200 according to another embodiment of the invention is shown. Like test port assemblies 10 and 100, test port assembly 200 includes first and second end sections 211 and 212, a rotating section 213, and a test port 220 having a valve 221. The test port assembly 200 is also installed and operated like test port assemblies 10 and 100. Unlike test port assemblies 10 and 100, test port assembly 200 uses bearings 250 and 251 instead of supports and seals.

Bearing 250 is positioned between the first end section 211 and the rotating section 213, and includes an inner ring 252 and an outer ring 253 to allow rotation of the rotating section 213. As illustrated in FIG. 6, the bearing 250 is sandwiched between flanges 256 and 257. Flange 256 is connected to the first end section 211 and flange 257 is connected to the rotating section 213. The inner ring 252 is bolted to flange 256 and the outer ring is bolted to flange 257. Bearing 251 is sandwiched between the second end section 212 and the rotating section 213, and also includes an inner ring 258 bolted to a flange 261 connected to the second end section 212 and an outer ring 259 bolted to a flange 260 connected to the rotating section 213.

The bearings 250 and 251 allow the rotating section 213 to rotate easily between the first and second end sections 211 and 213. Because the bearings 250 and 251 are bolted to flanges, the bearings 250 and 251 support and align the assembly 200, thereby eliminating the need for supports like those used in assemblies 10 and 100. Because the bearings 250 and 251 support the assembly 200, they provide the ability to rotate the test port 220 three hundred and sixty degrees, thereby allowing a test probe to provide measurements around the entire conduit 217.

The foregoing has described a test port assembly. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A test port assembly, comprising:
   (a) a first end section;
   (b) a second end section;

(c) a rotating section adapted for rotation about the central axis of a conduit and positioned between the first and second end sections; and (d) a test port positioned on the rotating section for allowing a test probe to be inserted into a stream flowing in said conduit.

2. The test port assembly according to claim 1, wherein the test port includes a valve to prevent the stream from exiting the conduit through the test port.

3. The test port assembly according to claim 1, wherein the first end section is connected to a first end of the conduit and the second end section is connected to a second end of the conduit such that the test port assembly is aligned with the conduit.

4. The test port assembly according to claim 1, wherein at least one support is connected to the first and second end sections to support and align the test port assembly.

5. The test port assembly according to claim 1, further including at least one seal to prevent the stream from exiting the conduit through joints formed between the first end section and the rotating section and the second end section and the rotating section.

6. The test port assembly according to claim 1, further including a gear for rotating the rotating section.

7. The test port assembly according to claim 1, further including a handle positioned on the rotating section to aid in the rotation of the rotating section.

8. The test port assembly according to claim 1, further including a first sleeve extending from the first end section and a second sleeve extending from the second end section, such that a portion of the rotating section is positioned within the first and second sleeves.

9. The test port assembly according to claim 8, further including at least one seal positioned between the first sleeve and the rotating section and at least one seal positioned between the second sleeve and the rotating section to prevent the stream from exiting between the sleeves and the rotating section.

10. The test port assembly according to claim 1, further including a first bearing positioned between the first end section and the rotating section and a second bearing positioned between the second end section and the rotating section to permit the rotating section to rotate.

11. The test port assembly according to claim 10, wherein the first and second bearings each include an outer ring and an inner ring, the outer and inner rings being connected to flanges positioned on the first end section, the second end section, and the rotating section by fasteners.

12. A method for testing a stream in a conduit, comprising the steps of:

(a) replacing a section of the conduit with a test port assembly, having:
  (i) a first end section;
  (ii) a second end section;
  (iii) a rotating section adapted for rotation about the central axis of the conduit and positioned between the first and second end sections; and
  (iv) a test port positioned on the rotating section;

(b) inserting a test probe into the test port until the probe is positioned at a desired location within the stream; and (c) rotating the rotating section to extract data from the test probe at various data points within the conduit.

13. The method according to claim 12, further including the step of opening a valve of the test port to allow access to the stream.

14. The method according to claim 12, further including the step of closing a valve of the test port to prevent the stream from exiting the conduit through the test port.

* * * * *